United States Patent [19]

Bayless et al.

[11] 4,242,325

[45] Dec. 30, 1980

[54] PHOSPHOROTRIAMIDES AS UREASE INHIBITORS

[75] Inventors: Allan V. Bayless; Ozra E. Millner, Jr., both of Norwich, N.Y.

[73] Assignee: Morton-Norwich Products, Inc., Norwich, N.Y.

[21] Appl. No.: 55,459

[22] Filed: Jul. 6, 1979

[51] Int. Cl.$^3$ ............................................. A61K 31/66
[52] U.S. Cl. .................................. 424/210; 424/211; 424/218; 424/220
[58] Field of Search ................ 424/210, 211, 218, 220

[56] References Cited

FOREIGN PATENT DOCUMENTS 741662  12/1955  United Kingdom ..................... 424/220

OTHER PUBLICATIONS

*The Enzymes,* vol. 1, Part 2, pp. 882–885, 1951 Academic Press, Inc., Pub. New York.
*The Chemistry and Technology of Enzymes,* pp. 119–120 Tauber, John Wiley & Sons, Inc. New York
*Inorganic Synthesis,* 6:108–111, Klement et al.
*Bull. Chem. Soc.,* Japan 46:183 (1973).

*Primary Examiner*—Frederick E. Waddell
*Attorney, Agent, or Firm*—Anthony J. Franze

[57] ABSTRACT

Certain phosphorotriamides of the formula

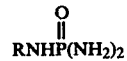

wherein R is hydrogen, phenyl, 4-nitrophenyl, 4-aminophenyl, 4-cyanophenyl or 3-trifluromethylphenyl are useful as inhibitors of the enzyme urease.

1 Claim, No Drawings

PHOSPHOROTRIAMIDES AS UREASE INHIBITORS

This invention is concerned with the use of phosphorotriamides of the formula

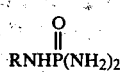
RNHP(NH$_2$)$_2$ wherein R is hydrogen, phenyl, 4-nitrophenyl, 4-aminophenyl, 4-cyanophenyl or 3-trifluromethylphenyl as potent inhibitors of the enzyme urease.

Urease is produced by a number of bacterial species particularly Proteus exemplary of which are *Proteus mirabilis, Proteus vulgaris, Proteus morganii* and *Proteus rettgeri*, all of which are well-known urinary tract pathogens. Their ability to produce urease in the urinary tract, which contains substantial amounts of urea, provides a setting wherein urease splits urea according to this scheme:

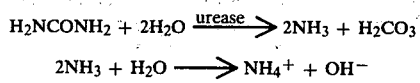

This reaction sequence poses a hyperammonuria and alkalinity of the urine affording a locale favorable to the formation of struvite (MgNH$_4$PO$_4$.6H$_2$O) a predominant component of infected urinary calculi. Such struvite formation and alkalinization of the urine render the treatment of urinary tract infections difficult and oftentimes recalcitrant to otherwise effective urinary tract antiseptics.

The phosphorotriamides with which this invention is concerned contain known members. Thus, when R=hydrogen or phenyl, their preparation has been previously described; Inorganic Syntheses 6:108 and Bull. Chem. Soc. Japan 46:183–6 (1973), respectively. Otherwise their preparation is in accordance with the following scheme:

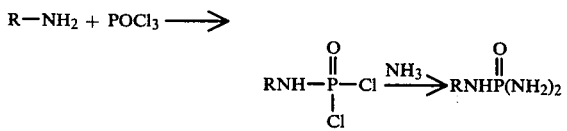

except for the amino derivative which is prepared by catalytic reduction of the corresponding nitro compound. The following examples are illustrative.

EXAMPLE I

N-(4-Nitrophenyl)phosphorotriamide

A. 4-Nitrophenylaminophosphoryl dichloride

To 300 ml of phosphorous oxychloride was carefully added 69 g (0.5 m) of 4-nitroaniline. The mixture was heated at reflux for 3 hours, then chilled to 10°. The crude product was collected by filtration, washed with ether and air-dried to give 93.6 g, m.p. 156.5°–157.5°.

B. N-(4-Nitrophenyl)phosphorotriamide

To a solution of 56.2 g (3.3 m) of anhydrous ammonia in 800 ml of AR methanol was added portionwise 83.6 g (0.33 m) of 4-nitrophenylaminophosphoryl dichloride. A temperature of −10° was maintained throughout the addition period of 90 mins. The reaction mixture was concentrated to dryness in vacuo at 50°. The white residue was slurried with cold distilled water, filtered and air-dried to give 69.3 g, m.p. 178°–180°. Recrystallization from 1700 ml of absolute alcohol gave 20.9 g (29.3%), m.p. softens 176°, melts 179.5°–180.5°.

Anal. Calcd. for C$_6$H$_9$N$_4$O$_3$P: C, 33.34; H, 4.20; N, 25.93. Found: C, 33.44; H, 4.11; N, 25.75.

EXAMPLE II

N-(4-Aminophenyl)phosphorotriamide

A mixture of 35 g (0.16 m) of N-(4-nitrophenyl)phosphorotriamide and 800 ml of absolute alcohol was reduced with hydrogen using 5.0 g of 5% Pd/C containing 50% water. A hydrogen uptake of 29.5 psi was recorded (theoretical 32.5 psi). The catalyst was removed by filtration and the ethanol filtrate concentrated to dryness in vacuo. The crude product was recrystallized from 1000 ml of methanol, with Darco, to yield 12.2 g (41%), m.p. 171°–173°.

Anal. Calcd. for C$_6$H$_{11}$N$_4$OP: C, 38.71; H, 5.96; H, 30.10. Found: C, 38.63; H, 6.05; N, 29.88.

EXAMPLE III

N-(4-Cyanophenyl)phosphorotriamide

A. N-(4-Cyanophenyl)aminophosphoryl dichloride

A mixture of 39 g (0.33 m) of 4-aminobenzonitrile and 250 ml of POCl$_3$ was heated under reflux for 3 hours. The excess POCl$_3$ was removed by vacuum distillation to yield 72.7 g, m.p. softens 128°, melts 131°–133.5°.

B. N-(4-Cyanophenyl)phosphorotriamide

To a solution of 49.3 g (2.9 m) of anhydrous ammonia in 500 ml of AR chloroform was added dropwise at 0° over 30 mins., a solution of 68 g (0.29 m) of N-(4-cyanophenyl)aminophosphoryl dichloride in 500 ml chloroform. The reaction mixture was stirred overnight at room temperature. The white precipitate was collected by filtration, washed thoroughly with cold water and air-dried to give 69.9 g. Recrystallization from 500 ml of ethanol gave 45 g (79%), m.p. 164°–167°.

Anal. Calcd. for C$_7$H$_9$N$_4$OP: C, 42.86; H, 4.62; N, 28.57. Found: C, 42.83; H, 4.64; N, 28.49.

EXAMPLE IV

N-[3-(Trifluoromethyl)phenyl]phosphorotriamide

A. N-[3-(Trifluoromethyl)phenyl]aminophosphoryl dichloride

To a solution of 60 g (0.37 m) of 3-trifluoromethylaniline and 300 ml of POCl$_3$ was heated at reflux for 3 hours. The excess POCl$_3$ was removed by vacuum distillation to yield 102 g of a red-brown oil.

B. N-[3-(Trifluoromethyl)phenyl]phosphorotriamide

To a solution of 50 g (0.18 m) of N-[3-(trifluoromethyl)phenyl]aminophosphoryl dichloride in 500 ml of chloroform was added 31 g (1.8 m) of anhydrous ammonia. A temperature of −10° was maintained throughout the 45 min. addition. After stirring for an additional 60 mins., the crude product was collected, washed with cold water and air-dried to give 53.5 g, m.p. softens 150°, some melts 153°–157°. Recrystallization from 325 ml of distilled water, with Darco, gave 26.5 g, melts 149°–152°.

Anal. Calcd. for $C_7H_9F_3N_3OP$: C, 35.01; H, 3.78; N, 17.50. Found: C, 35.18; H, 3.75; N, 17.67.

The urease inhibiting propensity present in the phosphorotriamides is exemplified below:

The Inhibition of Urease Purified from *Proteus mirabilis* (Pr-91)

Concentration of Compounds of Formula

for 50% Inhibition of Urease.

| Compound (R=) | Concentration |
|---|---|
| H | $1.2 \times 10^{-7}$M |
| Phenyl | $1.3 \times 10^{-5}$M |
| 4-Nitrophenyl | $3.5 \times 10^{-7}$M |
| 4-Aminophenyl | $1.6 \times 10^{-5}$M |
| 4-Cyanophenyl | $5.0 \times 10^{-5}$M |

-continued

| Compound (R=) | Concentration |
|---|---|
| 3-Trifluoromethylphenyl | $4.0 \times 10^{-5}$M |

For ease and convenience of application the phosphorotriamides are admixed with suitable excipients, adjuvants and additives providing formulations such as tablets, elixirs, suspensions, dusts and the like, each containing sufficient active ingredient to exert urease inhibiting activity.

What is claimed is:

1. A method for controlling the enzymatic decomposition of urea to ammonia and carbonic acid due to the action of the enzyme urease thereon which consists in exposing said enzyme to an amount of a compound of the formula

wherein R is hydrogen, phenyl, 4-nitrophenyl, 4-aminophenyl, 4-cyanophenyl or 3-trifluoromethylphenyl sufficient to inhibit said enzymatic decomposition.

* * * * *